(12) United States Patent
Ruchelman et al.

(10) Patent No.: US 9,303,014 B2
(45) Date of Patent: Apr. 5, 2016

(54) SYNTHESIS OF 3-(5-AMINO-2-METHYL-4-OXOQUINAZOLIN-3(4H)-YL)PIPERIDINE-2,6-DIONE

(71) Applicant: Celgene Corporation, Summit, NJ (US)

(72) Inventors: Alexander L. Ruchelman, Cream Ridge, NJ (US); Benjamin M. Cohen, Cranford, NJ (US); Anusuya Choudhury, Churchville, PA (US); Matthew M. Kreilein, Hillsborough, NJ (US); William W. Leong, Westfield, NJ (US); Hon-Wah Man, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/864,614

(22) Filed: Sep. 24, 2015

(65) Prior Publication Data

US 2016/0009685 A1 Jan. 14, 2016

Related U.S. Application Data

(60) Division of application No. 14/736,146, filed on Jun. 10, 2015, which is a continuation of application No. 14/266,448, filed on Apr. 30, 2014, now Pat. No. 9,067,912.

(60) Provisional application No. 61/818,254, filed on May 1, 2013.

(51) Int. Cl.
*C07D 401/04* (2006.01)

(52) U.S. Cl.
CPC .................................. *C07D 401/04* (2013.01)

(58) Field of Classification Search
CPC ....................................................... C07D 401/04
See application file for complete search history.

(56) References Cited

U.S. PATENT DOCUMENTS

| 7,635,700 B2 * | 12/2009 | Muller | C07D 401/14 514/266.22 |
| 2012/0232100 A1 | 9/2012 | Muller et al. | |
| 2014/0228382 A1 * | 8/2014 | DeWitt | C07D 401/04 514/266.22 |

FOREIGN PATENT DOCUMENTS

WO 2014039421 A1 3/2014

OTHER PUBLICATIONS

Gowda et al., "Formic acid with 10% palladium on carbon: A reagent for selective reduction of aromatic nitro compounds," Indian J. Chem., Sect. B: Org. Chem. Incl. Med. Chem. 2000, 59B:709-711.

* cited by examiner

*Primary Examiner* — Sun Jae Yoo
(74) *Attorney, Agent, or Firm* — Jones Day

(57) ABSTRACT

Provided herein are processes for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt thereof.

3 Claims, No Drawings

SYNTHESIS OF 3-(5-AMINO-2-METHYL-4-OXOQUINAZOLIN-3(4H)-YL)PIPERIDINE-2,6-DIONE

I. CROSS REFERENCE TO RELATED APPLICATION

This application is a divisional application of U.S. application Ser. No. 14/736,146, filed Jun. 10, 2015; which is a continuation application of U.S. application Ser. No. 14/266,448, filed Apr. 30, 2014; which claims the benefit of U.S. Provisional Patent Application No. 61/818,254, filed May 1, 2013; the disclosure of each of which is incorporated herein by reference in its entirety.

II. FIELD

Provided herein are processes for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

III. BACKGROUND

Many types of cancers are associated with new blood vessel formation, a process known as angiogenesis. Several mechanisms involved in tumor-induced angiogenesis have been elucidated. The most direct of these mechanisms is the secretion by the tumor cells of cytokines with angiogenic properties, including tumor necrosis factor α (TNF-α).

A variety of other diseases and disorders are also associated with or characterized by undesired angiogenesis. For example, enhanced or unregulated angiogenesis has been implicated in a number of diseases and medical conditions, including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to, diabetic retinopathy, retinopathy of prematurity, corneal graft rejection, neovascular glaucoma, retrolental fibroplasia, arthritis, and proliferative vitreoretinopathy.

Certain 4-oxoquinazoline compounds, including 3-(5-amino-2-methyl-4-oxoquinazolin-3(4H)-yl)piperidine-2,6-dione, have been reported to be capable of controlling angiogenesis or inhibiting the production of certain cytokines, including TNF-α, and useful in the treatment and prevention of various diseases and conditions. See U.S. Pat. No. 7,635,700, the disclosure of which is incorporated herein by reference in its entirety.

A method for synthesizing 3-(5-amino-2-methyl-4-oxoquinazolin-3(4H)-yl)piperidine-2,6-dione has been described in U.S. Pat. No. 7,635,700. A need still exists for efficient and scalable processes for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

IV. SUMMARY

Provided herein are, inter alia, safe, efficient, cost effective, and/or readily scalable methods for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

Methods provided herein are generally directed to: (a) reacting 2-amino-6-nitrobenzoic acid under conditions suitable to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione under conditions suitable to form 3-(2-methyl-5-nitro-4-oxoquinazolin-3(4H)-yl)piperidine-2,6-dione; and (c) reducing 3-(2-methyl-5-nitro-4-oxoquinazolin-3(4H)-yl)piperidine-2,6-dione under conditions suitable to form 3-(5-amino-2-methyl-4-oxoquinazolin-3(4H)-yl)piperidine-2,6-dione.

Also provided herein is N-(3-(2,6-dioxopiperidin-3-yl)-2-methyl-4-oxo-3,4-dihydroquinazolin-5-yl)formamide, or an enantiomer or a mixture of enantiomers thereof; or a solvate, hydrate, or polymorph thereof.

Further provided herein is a method for preparing N-(3-(2,6-dioxopiperidin-3-yl)-2-methyl-4-oxo-3,4-dihydroquinazolin-5-yl)formamide, or an enantiomer or a mixture of enantiomers thereof; or a solvate, hydrate, or polymorph thereof; comprising the step of reducing 3-(2-methyl-5-nitro-4-oxoquinazolin-3(4H)-yl)piperidine-2,6-dione in the presence of formic acid to form N-(3-(2,6-dioxopiperidin-3-yl)-2-methyl-4-oxo-3,4-dihydroquinazolin-5-yl)formamide, or an enantiomer or a mixture of enantiomers thereof; or a solvate, hydrate, or polymorph thereof.

V. DETAILED DESCRIPTION

Unless defined otherwise, all technical and scientific terms used herein have the same meaning as those commonly understood by one of ordinary skill in the art. All publications and patents referred to herein are incorporated by reference herein in their entireties.

A. Definitions

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs.

The term "alkyl" refers to a linear or branched saturated monovalent hydrocarbon radical, wherein the alkyl is optionally substituted with one or more substituents Q as described herein elsewhere. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s), wherein the alkenyl is optionally substituted with one or more substituents Q as described herein elsewhere. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s), wherein the alkynyl is optionally substituted with one or more substituents Q as described herein elsewhere. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic monovalent hydrocarbon radical, wherein the cycloalkyl is optionally substituted with one or more substituents Q as described herein elsewhere. In one embodiment, cycloalkyl groups may be saturated or unsaturated but non-aromatic, and/or spiro, and/or non-spiro, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cycloheptenyl, bicyclo[2.1.1]hexyl, bicyclo[2.2.1]heptyl, decalinyl, and adamantyl.

The term "aryl" refers to a monovalent monocyclic aromatic group and/or monovalent polycyclic aromatic group that contain at least one aromatic carbon ring, wherein the aryl is optionally substituted with one or more substituents Q as described herein elsewhere. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. The term "aryl" also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl).

The term "aralkyl" or "arylalkyl" refers to a monovalent alkyl group substituted with one or more aryl groups, wherein the aralkyl or arylalkyl is optionally substituted with one or more substituents Q as described herein elsewhere. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 2-phenylethyl, and 3-phenylpropyl.

The term "heteroaryl" refers to a monovalent monocyclic aromatic group and/or monovalent polycyclic aromatic group that contain at least one aromatic ring, wherein at least one aromatic ring contains one or more heteroatoms independently selected from O, S, N, and P in the ring. Heteroaryl groups are bonded to the rest of a molecule through the aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein elsewhere.

The term "heterocyclyl" or "heterocyclic" refers to a monovalent monocyclic non-aromatic ring system and/or monovalent polycyclic ring system that contain at least one non-aromatic ring, wherein one or more of the non-aromatic ring atoms are heteroatoms independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of a molecule through the non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein elsewhere.

The term "alkene" refers to a linear or branched hydrocarbon, which contains one or more, in one embodiment, one to five, in another embodiment, one, carbon-carbon double bond(s), wherein the alkene is optionally substituted with one or more substituents Q as described herein elsewhere. The term "alkene" embraces a compound having a "cis" or "trans" configuration or a mixture thereof, or alternatively, a "Z" or "E" configuration or a mixture thereof, as appreciated by those of ordinary skill in the art. For example, $C_{2-6}$ alkene refers to a linear unsaturated hydrocarbon of 2 to 6 carbon atoms or a branched unsaturated hydrocarbon of 3 to 6 carbon atoms. In certain embodiments, the alkene is a linear hydrocarbon of 2 to 20 ($C_{2-20}$), 2 to 15 ($C_{2-15}$), 2 to 10 ($C_{2-10}$), or 2 to 6 ($C_{2-6}$) carbon atoms, or a branched hydrocarbon of 3 to 20 ($C_{3-20}$), 3 to 15 ($C_{3-15}$), 3 to 10 ($C_{3-10}$), or 3 to 6 ($C_{3-6}$) carbon atoms.

The term "cycloalkene" refers to a cyclic hydrocarbon, which contains one or more, in one embodiment, one to five, in another embodiment, one, carbon-carbon double bond(s), wherein the cycloalkene is optionally substituted with one or more substituents Q as described herein elsewhere. In one embodiment, the cycloalkene may be non-aromatic, and/or spiro, and/or non-spiro, and/or bridged, and/or non-bridged, and/or fused bicyclic. In certain embodiments, the cycloalkene has from 3 to 20 ($C_{3-20}$), from 3 to 15 ($C_{3-15}$), from 3 to 10 ($C_{3-10}$), or from 3 to 7 ($C_{3-7}$) carbon atoms.

The term "arene" refers to a monocyclic aromatic compound and/or polycyclic aromatic compound that contain at least one aromatic carbon ring, wherein the arene is optionally substituted with one or more substituents Q as described herein elsewhere. In certain embodiments, the arene has from 6 to 20 ($C_{6-20}$), from 6 to 15 ($C_{6-15}$), or from 6 to 10 ($C_{6-10}$) ring atoms. The term "arene" also refers to bicyclic or tricyclic carbon rings, where one of the rings is aromatic and the other(s) may be saturated, partially unsaturated, or aromatic.

The term "heteroarene" refers to a monocyclic aromatic and/or polycyclic aromatic compound that contain at least one aromatic ring, wherein at least one aromatic ring contains one or more heteroatoms independently selected from O, S, N, and P in the ring. Each ring of a heteroarene can contain one or two O atoms, one or two S atoms, one to four N atoms, and/or one or two P atoms, provided that the total number of heteroatoms in each ring is four or less and each ring contains at least one carbon atom. In certain embodiments, the heteroarene has from 5 to 20, from 5 to 15, or from 5 to 10 ring atoms. In certain embodiments, the heteroarene is optionally substituted with one or more substituents Q as described herein elsewhere.

The term "heterocycle" refers to a monocyclic non-aromatic ring system and/or non-aromatic polycyclic ring system, wherein one or more of the non-aromatic ring atoms are heteroatoms, each of which is independently selected from O, S, N, and P; and the remaining ring atoms are carbon atoms. In certain embodiments, the heterocycle has from 3 to 20, from 3 to 15, from 3 to 10, from 3 to 8, from 4 to 7, or from 5 to 6 ring atoms. In certain embodiments, the heterocycle is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated. In certain embodiments, the heterocycle is optionally substituted with one or more substituents Q as described herein elsewhere.

The term "alcohol" refers to alkyl-OH, alkenyl-OH, alkynyl-OH, cycloalkyl-OH, aryl-OH, aralkyl-OH, heteroaryl-OH, or heterocyclyl-OH, wherein the alkyl, alkenyl, alkynyl, cycloalkyl, aryl, aralkyl, heteroaryl, and heterocyclyl are each as defined herein.

The term "carboxylic acid" refers to alkyl-COOH, alkenyl-COOH, alkynyl-COOH, cycloalkyl-COOH, aryl-COOH, aralkyl-COOH, heteroaryl-COOH, or heterocyclyl-COOH, wherein the alkyl, alkenyl, alkynyl, cycloalkyl, aryl, aralkyl, heteroaryl, and heterocyclyl are each as defined herein.

The term "carboxylic acid ester" or "ester" refers to alkyl-COOR', alkenyl-COOR', alkynyl-COOR', cycloalkyl-COOR', aryl-COOR', aralkyl-COOR', heteroaryl-COOR', or heterocyclyl-COOR', and each R' is independently wherein alkyl, alkenyl, alkynyl, cycloalkyl, aryl, aralkyl, heteroaryl, and heterocyclyl; and wherein each alkyl, alkenyl, alkynyl, cycloalkyl, aryl, aralkyl, heteroaryl, and heterocyclyl is as defined herein.

The term "optionally substituted" is intended to mean that a group or substituent, such as an alkyl, alkenyl, alkynyl, cycloalkyl, aryl, aralkyl, heteroaryl, or heterocyclyl group, may be substituted with one or more substituents Q, each of which is independently selected from, e.g., (a) oxo (=O), halo, cyano (—CN), and nitro (—$NO_2$); (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (c) —C(O)$R^a$, —C(O)O$R^a$, —C(O)N$R^b R^c$, —C(N$R^a$)N$R^b R^c$, —O$R^a$, —OC(O)$R^a$, —OC(O)O$R^a$, —OC(O)N$R^b R^c$, —OC(=N$R^a$) N$R^b R^c$, —OS(O)$R^a$, —OS(O)$_2 R^a$, —OS(O)N$R^b R^c$, —OS(O)$_2$N$R^b R^c$, —N$R^b R^c$, —N$R^a$C(O)$R^d$, —N$R^a$C(O)O$R^d$, —N$R^a$C(O)N$R^b R^c$, —N$R^a$C(=N$R^d$)N$R^b R^c$, —N$R^a$S(O) $R^d$, —N$R^a$S(O)$_2 R^d$, —N$R^a$S(O)N$R^b R^c$, —N$R^a$S(O)$_2$N$R^b R^c$, —P(O)$R^a R^d$, —P(O)(O$R^a$)$R^d$, —P(O)(O$R^a$)(O$R^d$), —S$R^a$, —S(O)$R^a$, —S(O)$_2 R^a$, —S(O)N$R^b R^c$, and —S(O)$_2$ N$R^b R^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, or heterocyclyl, each of which is optionally substituted with one or more, in one embodiment, one, two, three, or four, substituents $Q^a$; or (iii) $R^b$ and $R^c$ together with the N atom to which they are attached form heteroaryl or heterocyclyl, each of which optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-10}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^h$, —N$R^e$C(O)O$R^h$, —N$R^e$C(O)N$R^f R^g$, —N$R^e$C(=N$R^h$)N$R^f R^g$, —N$R^e$S(O)$R^h$, —N$R^e$S(O)$_2 R^h$, —N$R^e$S(O)N$R^f R^g$, —N$R^e$S(O)$_2$N$R^f R^g$, —P(O)$R^e R^h$, —P(O)(O$R^e$)$R^h$, —P(O)

(OR$^e$)(OR$^h$), —SR$^e$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen, C$_{1-6}$ alkyl, C$_{2-6}$ alkenyl, C$_{2-6}$ alkynyl, C$_{3-10}$ cycloalkyl, C$_{6-14}$ aryl, C$_{7-15}$ aralkyl, heteroaryl, or heterocyclyl; or (ii) R$^f$ and R$^g$ together with the N atom to which they are attached form heteroaryl or heterocyclyl.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "substantially free" when referring to a composition that is "substantially free" of a compound refers means that the composition contains no greater than about 20% by weight, no greater than about 10% by weight, no greater than about 5% by weight, no greater than about 3% by weight, no greater than about 1% by weight, no greater than about 0.5% by weight, no greater than about 0.2% by weight, no greater than about 0.1% by weight, no greater than about 0.01% by weight, no greater than about 0.001% by weight, or no greater than about 0.0001% by weight of the compound.

The term "substantially pure" when referring to a compound or composition means that the compound or composition has a purity of no less than about 80% by weight, no less than about 90% by weight, no less than about 95% by weight, no less than about 96% by weight, no less than about 97% by weight, no less than about 98% by weight, no less than about 99% by weight, no less than about 99.5% by weight, no less than about 99.9% by weight, no less than about 99.95% by weight, no less than about 99.99% by weight, g no less than about 99.995% by weight, no less than about 99.999% by weight, no less than about 99.9995% by weight, or no less than about 99.9999% by weight.

The terms "process" and "method" are used interchangeably to refer to a method disclosed herein for a compound preparation. Modifications to the processes and methods disclosed herein (e.g., starting materials, reagents, protecting groups, solvents, temperatures, reaction times, and/or purification) that are well known to those of ordinary skill in the art are also encompassed by the disclosure.

The terms "adding" "reacting" and "mixing" are used interchangeably to refer to contacting one reactant, reagent, solvent, catalyst, or a reactive group with another reactant, reagent, solvent, catalyst, or reactive group. Unless otherwise specified, reactants, reagents, solvents, catalysts, and reactive groups can be added individually, simultaneously, or separately, and/or can be added in any order. They can be added in the presence or absence of heat, and can optionally be added under an inert atmosphere (e.g., N$_2$ or Ar). In certain embodiments, the term "reacting" can also refer to in situ formation or intra-molecular reaction where the reactive groups are in the same molecule.

The term "substantially complete" when referring to a reaction means that the reaction contains no greater than about 50%, no greater than about 40%, no greater than about 30%, no greater than about 20%, no greater than about 10%, no greater than about 5%, no greater than about 4%, no greater than about 3%, no greater than about 2%, no greater than about 1%, no greater than about 0.5%, no greater than about 0.1%, or no greater than about 0.05% of a starting material left.

If the stereochemistry of a structure or a portion thereof is not indicated, e.g., with bold or dashed lines, the structure or portion thereof is to be interpreted as encompassing all stereoisomers of the structure.

The phrase "an enantiomer or a mixture of enantiomers thereof; or a pharmaceutically acceptable salt, solvate, hydrate, or polymorph thereof" has the same meaning as the phrase "an enantiomer or a mixture of enantiomers of the compound referenced therein; a pharmaceutically acceptable salt, solvate, hydrate, or polymorph of the compound referenced therein; or a pharmaceutically acceptable salt, solvate, hydrate, or polymorph of an enantiomer or a mixture of enantiomers of the compound referenced therein."

B. Processes

1. Preparation of 3-(5-amino-2-methyl-4-oxoquinazolin-3(4H)-yl)piperidine-2,6-dione Provided herein are methods for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof. In certain embodiments, the methods provided herein are safe, efficient, cost effective, and/or readily scalable. In certain embodiments, the methods provided herein are suitable for the large scale or commercial production of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

In one embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the step of reducing 3-(2-methyl-5-nitro-4-oxoquinazolin-3(4H)-yl)piperidine-2,6-dione via transfer hydrogenation in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

In one embodiment, the transfer hydrogenation is conducted in the presence of a hydrogen donor. In another embodiment, the transfer hydrogenation is conducted in the presence of a catalyst. In yet another embodiment, the transfer hydrogenation is conducted in the presence of a hydrogen donor and a catalyst.

In certain embodiments, the hydrogen donor is (i) a C$_{1-14}$ alcohol, C$_{1-14}$ carboxylic acid, C$_{1-14}$ carboxylic acid salt, C$_{1-14}$ carboxylic acid ester, C$_{2-14}$ alkene, C$_{3-14}$ cycloalkene, C$_{6-14}$ arene, heteroarene, or heterocycle, each of which is optionally substituted with one or more substituents Q; or (ii) diazene (also known as diimine or diimide), hydrazine, hydroxylamine, or NaH$_2$PO$_2$.

In certain embodiments, the hydrogen donor is a $C_{1-14}$ alcohol, optionally substituted with one or more substituents Q. In certain embodiments, the hydrogen donor is a primary or secondary $C_{1-14}$ alcohol, each optionally substituted with one or more substituents Q. In certain embodiments, the hydrogen donor is a primary $C_{1-14}$ alcohol, optionally substituted with one or more substituents Q. In certain embodiments, the hydrogen donor is a secondary $C_{1-14}$ alcohol, optionally substituted with one or more substituents Q. In certain embodiments, the hydrogen donor is methanol, ethanol, propan-1-ol, propan-2-ol, butan-1-ol, butan-2-ol, cyclopentanol, cyclohexanol, benzylalcohol, a menthol, or a mixture thereof.

In certain embodiments, the hydrogen donor is a $C_{1-14}$ carboxylic acid, optionally substituted with one or more substituents Q. In certain embodiments, the hydrogen donor is a 2-hydroxy-$C_{1-14}$ carboxylic acid, optionally substituted with one or more substituents Q. In certain embodiments, the hydrogen donor is formic acid, lactic acid, ascorbic acid, mandelic acid, or a mixture thereof. In certain embodiments, the hydrogen donor is formic acid.

In certain embodiments, the hydrogen donor is a $C_{1-14}$ carboxylic acid salt, optionally substituted with one or more substituents Q. In certain embodiments, the hydrogen donor is a carboxylic acid amine salt, optionally substituted with one or more substituents Q. In certain embodiments, the hydrogen donor is a carboxylic acid amine salt, wherein the amine is an aromatic amine. In certain embodiments, the hydrogen donor is a carboxylic acid amine salt, wherein the amine is pyridine. In certain embodiments, the hydrogen donor is a carboxylic acid amine salt, wherein the amine is a non-aromatic amine. In certain embodiments, the hydrogen donor is a carboxylic acid amine salt, wherein the amine is a primary, secondary, or tertiary amine. In certain embodiments, the hydrogen donor is a carboxylic acid amine salt, wherein the amine is a primary amine. In certain embodiments, the hydrogen donor is a carboxylic acid amine salt, wherein the amine is a secondary amine. In certain embodiments, the hydrogen donor is a carboxylic acid amine salt, wherein the amine is a tertiary amine. In certain embodiments, the hydrogen donor is a carboxylic acid amine salt, wherein the amine is a tri-($C_{1-6}$ alkyl)amine. In certain embodiments, the hydrogen donor is a carboxylic acid amine salt, wherein the amine is a trimethylamine, triethylamine, di(isopropyl)ethylamine, pyridine, or a mixture thereof. In certain embodiments, the hydrogen donor is a $C_{1-14}$ carboxylic acid ammonium salt. In certain embodiments, the hydrogen donor is ammonium formate or potassium formate.

In certain embodiments, the hydrogen donor is a $C_{1-14}$ carboxylic acid ester.

In certain embodiments, the hydrogen donor is $C_{2-14}$ alkene, optionally substituted with one or more substituents Q. In certain embodiments, the hydrogen donor is a terpene.

In certain embodiments, the hydrogen donor is $C_{3-14}$ cycloalkene, optionally substituted with one or more substituents Q. In certain embodiments, the hydrogen donor is cyclohexadiene, cyclohexene, 1-methylcyclohexene, or a mixture thereof.

In certain embodiments the hydrogen donor is $C_{6-14}$ arene, optionally substituted with one or more substituents Q. In certain embodiments the hydrogen donor is tetralin.

In certain embodiments the hydrogen donor is a heteroarene, optionally substituted with one or more substituents Q.

In certain embodiments the hydrogen donor is a heterocycle, optionally substituted with one or more substituents Q. In certain embodiments the hydrogen donor is dihydrofuran.

In certain embodiments, the hydrogen donor is diazene, hydrazine, hydroxylamine, or $NaH_2PO_2$.

In certain embodiments, the hydrogen donor is methanol, ethanol, propan-1-ol, propan-2-ol, butan-1-ol, butan-2-ol, cyclopentanol, cyclohexanol, benzylalcohol, a menthol, formic acid, lactic acid, ascorbic acid, mandelic acid, ammonium formate, potassium formate, cyclohexadiene, cyclohexene, 1-methylcyclohexene, tetralin, dihydrofuran, a terpene, diazene, hydrazine, hydroxylamine, or $NaH_2PO_2$, or a mixture thereof. In certain embodiments, the hydrogen donor is formic acid, ammonium formate, potassium formate, cyclohexene, 1-methylcyclohexene, $NaH_2PO_2$, or a mixture thereof.

In certain embodiments, the catalyst is a hydrogenation catalyst. In certain embodiments, the catalyst is a heterogeneous hydrogenation catalyst. In certain embodiments, the catalyst is Raney nickel, palladium, palladium black, palladium on carbon (Pd/C), palladium oxide, Lindlar catalyst, platinum, platinum black, platinum on carbon (Pt/C), or platinum dioxide (also known as Adam's catalyst). In certain embodiments, the catalyst is a homogeneous hydrogenation catalyst. In certain embodiments, the homogeneous catalyst is an iridium-based catalyst. In certain embodiments, the homogeneous catalyst is a palladium-based catalyst. In certain embodiments, the homogeneous catalyst is a platinum-based catalyst. In certain embodiments, the homogeneous catalyst is a rhodium-based catalyst. In certain embodiments, the homogeneous catalyst is chloro-tris(triphenylphosphine)rhodium(I) (also known as Wilkinson's catalyst). In certain embodiments, the homogeneous catalyst is an iridium-based catalyst. In certain embodiments, the homogeneous catalyst is Crabtree's catalyst.

In certain embodiments, the catalyst is a precious metal catalyst. In certain embodiments, the catalyst is an iridium, palladium, platinum, rhodium, or ruthenium catalyst. In certain embodiments, the catalyst is an iridium catalyst. In certain embodiments, the catalyst is a palladium catalyst. In certain embodiments, the catalyst is palladium, palladium black, palladium on carbon (Pd/C), palladium oxide, or Lindlar catalyst. In certain embodiments, the catalyst is a platinum catalyst. In certain embodiments, the catalyst is palladium. In certain embodiments, the catalyst is palladium black. In certain embodiments, the catalyst is palladium on carbon (Pd/C). In certain embodiments, the catalyst is palladium oxide. In certain embodiments, the catalyst is Lindlar catalyst. In certain embodiments, the catalyst is a platinum catalyst. In certain embodiments, the catalyst is platinum, platinum black, platinum on carbon (Pt/C), or platinum dioxide. In certain embodiments, the catalyst is platinum. In certain embodiments, the catalyst is platinum black. In certain embodiments, the catalyst is platinum on carbon (Pt/C). In certain embodiments, the catalyst is platinum dioxide. In certain embodiments, the catalyst is a rhodium catalyst. In certain embodiments, the catalyst is a ruthenium catalyst.

In certain embodiments, the catalyst is a non-precious metal catalyst. In certain embodiments, the catalyst is a nickel catalyst. In certain embodiments, the catalyst is Raney nickel.

In certain embodiments, the solvent in the transfer hydrogenation is a hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent in the transfer hydrogenation is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl) ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in the transfer hydrogenation is a carboxylic acid. In certain embodiments, the solvent in the transfer hydrogenation is a mixture of a carboxylic acid and water. In certain embodiments, the volume ratio of the carboxylic acid versus water is ranging from about 0.1 to about 10, from about 0.2 to about 5, from about 0.5 to about 5, from about 0.5 to about 2, or from about 0.8 to about 1.5. In certain embodiments, the volume ratio of the carboxylic acid versus water is ranging from about 0.1 to about 10. In certain embodiments, the volume ratio of the carboxylic acid versus water is ranging from about 0.2 to about 5. In certain embodiments, the volume ratio of the carboxylic acid versus water is ranging from about 0.5 to about 5. In certain embodiments, the volume ratio of the carboxylic acid versus water is ranging from about 0.5 to about 2. In certain embodiments, the volume ratio of the carboxylic acid versus water is ranging from about 0.8 to about 1.5. In certain embodiments, the volume ratio of the carboxylic acid versus water is about 0.5, about 0.6, about 0.7, about 0.8, about 0.9, about 1, about 1.1, about 1.2, about 1.3, about 1.4, or about 1.5. In certain embodiments, the volume ratio of the carboxylic acid versus water is about 0.8, about 0.9, about 1, about 1.1, or about 1.2. In certain embodiments, the volume ratio of the carboxylic acid versus water is about 0.8. In certain embodiments, the volume ratio of the carboxylic acid versus water is about 0.9. In certain embodiments, the volume ratio of the carboxylic acid versus water is about 1. In certain embodiments, the volume ratio of the carboxylic acid versus water is about 1.1. In certain embodiments, the volume ratio of the carboxylic acid versus water is about 1.2.

In certain embodiments, the solvent in the transfer hydrogenation is formic acid. In certain embodiments, the solvent in the transfer hydrogenation is water.

In certain embodiments, the solvent in the transfer hydrogenation is a mixture of formic acid and water. In certain embodiments, the volume ratio of formic acid versus water is ranging from about 0.1 to about 10, from about 0.2 to about 5, from about 0.5 to about 5, from about 0.5 to about 2, or from about 0.8 to about 1.5. In certain embodiments, the volume ratio of formic acid versus water is ranging from about 0.1 to about 10. In certain embodiments, the volume ratio of formic acid versus water is ranging from about 0.2 to about 5. In certain embodiments, the volume ratio of formic acid versus water is ranging from about 0.5 to about 5. In certain embodiments, the volume ratio of formic acid versus water is ranging from about 0.5 to about 2. In certain embodiments, the volume ratio of formic acid versus water is ranging from about 0.8 to about 1.5. In certain embodiments, the volume ratio of formic acid versus water is about 0.5, about 0.6, about 0.7, about 0.8, about 0.9, about 1, about 1.1, about 1.2, about 1.3, about 1.4, or about 1.5. In certain embodiments, the volume ratio of formic acid versus water is about 0.8, about 0.9, about 1, about 1.1, or about 1.2. In certain embodiments, the volume ratio of formic acid versus water is about 0.8. In certain embodiments, the volume ratio of formic acid versus water is about 0.9. In certain embodiments, the volume ratio of formic acid versus water is about 1. In certain embodiments, the volume ratio of formic acid versus water is about 1.1. In certain embodiments, the volume ratio of formic acid versus water is about 1.2.

In certain embodiments, the molar ratio of formic acid versus 3-(2-methyl-5-nitro-4-oxoquinazolin-3(4H)-yl)piperidine-2,6-dione is ranging from about 1 to about 100, from about 2 to about 50, from about 5 to about 50, from about 5 to about 25, from about 10 to about 25, or from about 15 to about 25. In certain embodiments, the molar ratio of formic acid versus 3-(2-methyl-5-nitro-4-oxoquinazolin-3(4H)-yl)piperidine-2,6-dione is ranging from about 1 to about 100. In certain embodiments, the molar ratio of formic acid versus 3-(2-methyl-5-nitro-4-oxoquinazolin-3(4H)-yl)piperidine-2,6-dione is ranging from about 2 to about 50. In certain embodiments, the molar ratio of formic acid versus 3-(2-methyl-5-nitro-4-oxoquinazolin-3(4H)-yl)piperidine-2,6-dione is ranging from about 5 to about 50. In certain embodiments, the molar ratio of formic acid versus 3-(2-methyl-5-nitro-4-oxoquinazolin-3(4H)-yl)piperidine-2,6-dione is ranging from about 5 to about 25. In certain embodiments, the molar ratio of formic acid versus 3-(2-methyl-5-nitro-4-oxoquinazolin-3(4H)-yl)piperidine-2,6-dione is ranging from about 10 to about 25. In certain embodiments, the molar ratio of formic acid versus 3-(2-methyl-5-nitro-4-oxoquinazolin-3(4H)-yl)piperidine-2,6-dione is ranging from about 15 to about 25. In certain embodiments, the molar ratio of formic acid versus 3-(2-methyl-5-nitro-4-oxoquinazolin-3(4H)-yl)piperidine-2,6-dione is about 15, about 16, about 17, about 18, about 19, about 20, about 21, about 22, about 23, about 24, or about 25.

In certain embodiments, the transfer hydrogenation is performed at a temperature ranging from about 0 to about 100° C., from about 5 to about 90° C., from about 5 to about 80° C., from about 10 to about 70° C., or from about 10 to about 60° C.

In certain embodiments, when the hydrogen donor is formic acid, the transfer hydrogenation further comprises the step of hydrolyzing N-(3-(2,6-dioxopiperidin-3-yl)-2-methyl-4-oxo-3,4-dihydroquinazolin-5-yl)formamide to form 3-(5-amino-2-methyl-4-oxoquinazolin-3(4H)-yl)piperidine-2,6-dione as described herein elsewhere.

In another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; and (b) reducing 3-(2-methyl-5-nitro-4-oxoquinazolin-3(4H)-yl)piperidine-2,6-dione in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

In certain embodiments, the 3-aminopiperidine-2,6-dione or a salt thereof in step (a) (i.e., reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is free 3-aminopiperidine-2,6-dione. In certain embodiments, the 3-aminopiperidine-2,6-dione or a salt thereof in step (a) is a salt of 3-aminopiperidine-2,6-dione. In certain embodiments, the 3-aminopiperidine-2,6-dione or a salt thereof in step (a) is 3-aminopiperidine-2,6-dione hydrochloride.

In certain embodiments, the coupling reagent in step (a) (i.e., reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is a carbodiimide, 1,1'-carbonyldiimidazole (CDI), bis(2-oxo-3-oxazolidinyl)phosphinic chloride (BOP-Cl), O-(7-azabenzotriazol-1-yl)-N,N,N',N'-tetramethyluronium hexafluorophosphate (HATU), (7-azabenzotriazol-1-yloxy)tripyrrolidinophosphonium hexafluorophosphate (PyAOP), (benzotriazol-1-yloxy)tripyrrolidinophosphonium hexafluorophosphate (PyBOP), (benzotriazol-1-yloxy)tris(dimethylamino)phosphonium hexafluorophosphate (BOP reagent), N,N,N',N'-tetramethyl-O-(1H-benzotriazol-1-yl)uronium hexafluorophosphate (HBTU), O-(benzotriazol-1-yl)-N,N,N',N'-tetramethyluronium tetrafluoroborate (TBTU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate, $PCl_3$, $PCl_5$, or 1-propanephosphonic acid cyclic anhydride. In certain embodiments, the coupling reagent in step (a) is N-(3-dimethylaminopropyl)-N'-ethylcarbodiimide (EDC or EDCI), N-(3-dimethylaminopropyl)-N'-ethylcarbodiimide hydrochloride (EDC hydrochloride), 1-[3-(dimethylamino)propyl]-3-ethylcarbodiimide methiodide (EDC methiodide), 1-cyclohexyl-3-(2-morpholinoethyl)carbodiimide metho-p-toluenesulfonate, or 1,3-dicyclohexylcarbodiimide (DCC). In certain embodiments, the coupling reagent in step (a) is $PCl_3$, $PCl_5$, 1-propanephosphonic acid cyclic anhydride, $POCl_3$, or a mixture of $POCl_3$ and water. In certain embodiments, the coupling reagent in step (a) contains $PCl_3$, $PCl_5$, 1-propanephosphonic acid cyclic anhydride, acetic anhydride, phosphoric acid, $POCl_3$, or a mixture of $POCl_3$ and water. In certain embodiments, the coupling reagent in step (a) is 1-propanephosphonic acid cyclic anhydride. In certain embodiments, the coupling reagent in step (a) contains acetic anhydride. In certain embodiments, the coupling reagent in step (a) contains acetic anhydride and phosphoric acid. In certain embodiments, the coupling reagent in step (a) is a mixture of acetic anhydride and phosphoric acid. In certain embodiments, the coupling reagent in step (a) contains $POCl_3$. In certain embodiments, the coupling reagent in step (a) contains $POCl_3$ and water. In certain embodiments, the coupling reagent in step (a) is a mixture of $POCl_3$ and water. In certain embodiments, the molar ratio of $POCl_3$ versus water is ranging from about 0.5 to about 5; from about 0.7 to about 4; or from about 1 to about 3. In certain embodiments, the molar ratio of $POCl_3$ versus water is about 1, about 1.5, about 2, or about 3.

In certain embodiments, the solvent in step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is a hydrocarbon, chlorinated hydrocarbon, alcohol, ether, ketone, ester, carbonate, amide, nitrile, sulfoxide, sulfone, nitro compound, arene, heteroarene, heterocycle, carboxylic acid, phosphoramide, carbon sulfide, water, or a mixture thereof.

In certain embodiments, the solvent in step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is a nitrile. In certain embodiments, the solvent in step (a) is a carboxylic acid ester. In certain embodiments, the solvent in step (a) is a mixture of a nitrile and carboxylic acid ester. In certain embodiments, the solvent in step (a) is an amide. In certain embodiments, the solvent in step (a) is a cyclic amide. In certain embodiments, the solvent in step (a) is 1-methyl-2-pyrrolidone (NMP), acetonitrile, THF, or 2-methyl-THF. In certain embodiments, the solvent in step (a) is NMP. In certain embodiments, the volume ratio of the nitrile versus carboxylic acid ester is ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of the nitrile versus carboxylic acid ester is ranging from about 0.1 to about 100. In certain embodiments, the volume ratio of the nitrile versus carboxylic acid ester is ranging from about 0.2 to about 50. In certain embodiments, the volume ratio of the nitrile versus carboxylic acid ester is ranging from about 0.5 to about 25. In certain embodiments, the volume ratio of the nitrile versus carboxylic acid ester is ranging from about 1 to about 20. In certain embodiments, the volume ratio of the nitrile versus carboxylic acid ester is ranging from about 1 to about 10. In certain embodiments, the volume ratio of the nitrile versus carboxylic acid ester is ranging from about 1 to about 5. In certain embodiments, the volume ratio of the nitrile versus carboxylic acid ester is ranging from about 1 to about 2. In certain embodiments, the volume ratio between acetonitrile and ethyl acetate is about 1, about 1.1, about 1.2, about 1.3, about 1.4, about 1.5, about 1.6, about 1.7, about 1.8, about 1.9, or about 2.

In certain embodiments, the solvent in step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is acetonitrile. In certain embodiments, the solvent in step (a) is ethyl acetate. In certain embodiments, the solvent in step (a) is a mixture of acetonitrile and ethyl acetate. In certain embodiments, the volume ratio of acetonitrile versus ethyl acetate is ranging from about 0.1 to about 100, from about 0.2 to about 50, from about 0.5 to about 25, from about 1 to about 20, from about 1 to about 10, from about 1 to about 5, or from about 1 to about 2. In certain embodiments, the volume ratio of acetonitrile versus ethyl acetate is ranging from about 0.1 to about 100. In certain embodiments, the volume ratio of acetonitrile versus ethyl acetate is ranging from about 0.2 to about 50. In certain embodiments, the volume ratio of acetonitrile versus ethyl acetate is ranging from about 0.5 to about 25. In certain embodiments, the volume ratio of acetonitrile versus ethyl acetate is ranging from about 1 to about 20. In certain embodiments, the volume ratio of acetonitrile versus ethyl acetate is ranging from about 1 to about 10. In certain embodiments, the volume ratio of acetonitrile versus ethyl acetate is ranging from about 1 to about 5. In certain embodiments, the volume ratio of acetonitrile versus ethyl acetate is ranging from about 1 to about 2. In certain embodiments, the volume ratio of acetonitrile versus ethyl acetate is about 1, about 1.1, about 1.2, about 1.3, about 1.4, about 1.5, about 1.6, about 1.7, about 1.8, about 1.9, or about 2.

In certain embodiments, the molar ratio of the coupling reagent versus 2-methyl-5-nitro-4H-benzo[d][1,3]oxazin-4-one in step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is ranging from about 1 to about 10, from about 1 to about 5, or from about 1 to about 3. In certain embodiments, the molar ratio of the coupling reagent versus 2-methyl-5-nitro-4H-benzo[d][1,3]oxazin-4-one is ranging from about 1 to about 10. In certain embodiments, the molar ratio of the coupling reagent versus 2-methyl-5-nitro-4H-benzo[d][1,3]oxazin-4-one is ranging from about 1 to about 5. In certain embodiments, the molar ratio of the coupling reagent versus 2-methyl-5-nitro-4H-benzo[d][1,3]oxazin-4-one is ranging from about 1 to about 3. In certain embodiments, the molar ratio of the coupling reagent versus 2-methyl-5-nitro-4H-benzo[d][1,3]oxazin-4-one is about 1, about 1.5, about 2, about 2.5 or about 3.

In certain embodiments, step (a) (reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is conducted at a temperature ranging from about 0 to about 150° C., from about 25 to about 120° C., from about 50 to about 100° C., from about 60 to about 100° C., from about 70 to about 90° C., from about 70 to about 85° C., or from about 75 to about 80° C. In certain embodiments, step (a) is conducted at a temperature from about 75 to about 80° C.

In certain embodiments, the reduction of 3-(2-methyl-5-nitro-4-oxoquinazolin-3(4H)-yl)piperidine-2,6-dione to 3-(5-amino-2-methyl-4-oxoquinazolin-3(4H)-yl)piperidine-2,6-dione) in step (b) is via a transfer hydrogenation as described herein elsewhere. In certain embodiments, the reduction in step (b) is via catalytic hydrogenation. In certain embodiments, the reduction in step (b) is via catalytic hydrogenation under a hydrogen atmosphere. In certain embodiments, the reduction in step (b) is via catalytic hydrogenation in the presence of hydrogen gas ($H_2$). In certain embodiments, the reduction in step (b) is performed via catalytic hydrogenation in the presence of hydrogen gas and a palladium catalyst. In certain embodiments, the reduction in step (b) is performed via catalytic hydrogenation according to the procedures as described in U.S. Pat. No. 7,635,700, the disclosure of which is incorporated by reference in its entirety.

In certain embodiments, the reduction of 3-(2-methyl-5-nitro-4-oxoquinazolin-3(4H)-yl)piperidine-2,6-dione to 3-(5-amino-2-methyl-4-oxoquinazolin-3(4H)-yl)piperidine-2,6-dione is performed at a temperature ranging from about 0 to about 100° C., from about 5 to about 90° C., from about 5 to about 85° C., from about 10 to about 90° C., or from about 10 to about 85° C.

In yet another embodiment, provided herein is a method for preparing 3-(5-amino-2-methyl-4-oxoquinazolin-3(4H)-yl)piperidine-2,6-dione, or an enantiomer or a mixture of enantiomers thereof or a pharmaceutically acceptable salt, solvate, hydrate, or polymorph thereof comprising the steps of (a) reacting 2-methyl-5-nitro-4H-benzo[d][1,3]oxazin-4-one with 3-aminopiperidine-2,6-dione or a salt thereof in a solvent to form 3-(2-methyl-5-nitro-4-oxoquinazolin-3(4H)-yl)piperidine-2,6-dione; and (b) reducing 3-(2-methyl-5-nitro-4-oxoquinazolin-3(4H)-yl)piperidine-2,6-dione via transfer hydrogenation in a solvent to form 3-(5-amino-2-methyl-4-oxoquinazolin-3(4H)-yl)piperidine-2,6-dione, or an enantiomer or a mixture of enantiomers thereof or a pharmaceutically acceptable salt, solvate, hydrate, or polymorph thereof.

In certain embodiments, step (a) (i.e., reacting 2-methyl-5-nitro-4H-benzo[d][1,3]oxazin-4-one with 3-aminopiperidine-2,6-dione or a salt thereof to form 3-(2-methyl-5-nitro-4-oxoquinazolin-3(4H)-yl)piperidine-2,6-dione) is performed in the presence of a coupling reagent as described herein elsewhere. In certain embodiments, step (a) is performed by reacting 2-methyl-5-nitro-4H-benzo[d][1,3]oxazin-4-one with 3-aminopiperidine-2,6-dione or a salt thereof in the presence of a base. In certain embodiments, the base is an organic base. In certain embodiments, the base is an inorganic base. In certain embodiments, the base is sodium hydrogen carbonate, sodium carbonate, sodium citrate, dihydrate, sodium acetate, imidazole, or pyridine. In certain embodiments, step (a) is performed by reacting 2-methyl-5-nitro-4H-benzo[d][1,3]oxazin-4-one with 3-aminopiperidine-2,6-dione or a salt thereof in the presence of pyridine, according to the procedure as described in U.S. Pat. No. 7,635,700, the disclosure of which is incorporated by reference in its entirety.

In certain embodiments, the 3-aminopiperidine-2,6-dione or a salt thereof in step (a) (i.e., reacting 2-methyl-5-nitro-4H-benzo[d][1,3]oxazin-4-one and 3-aminopiperidine-2,6-dione or a salt thereof to form 3-(2-methyl-5-nitro-4-oxoquinazolin-3(4H)-yl)piperidine-2,6-dione) is free 3-aminopiperidine-2,6-dione. In certain embodiments, the 3-aminopiperidine-2,6-dione or a salt thereof in step (a) is a salt of 3-aminopiperidine-2,6-dione. In certain embodiments, the 3-aminopiperidine-2,6-dione or a salt thereof in step (a) is 3-aminopiperidine-2,6-dione hydrochloride.

In certain embodiments, step (b) (i.e., the transfer hydrogenation) is performed as described herein elsewhere.

In one specific embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; and (b) reducing 3-(2-methyl-5-nitro-4-oxoquinazolin-3(4H)-yl)piperidine-2,6-dione via transfer hydrogenation in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof, wherein steps (a) and (b) are each as described herein elsewhere.

In yet another embodiment, provided herein is a method for preparing 3-(5-amino-2-methyl-4-oxoquinazolin-3(4H)-yl) piperidine-2,6-dione, or an enantiomer or a mixture of enantiomers thereof or a pharmaceutically acceptable salt, solvate, hydrate, or polymorph thereof; comprising the steps of (a) reacting 2-amino-6-nitrobenzoic acid with an activated acetic acid in a solvent to form 2-methyl-5-nitro-4H-benzo[d][1,3] oxazin-4-one; (b) reacting 2-methyl-5-nitro-4H-benzo[d][1,3]oxazin-4-one with 3-aminopiperidine-2,6-dione or a salt thereof in a solvent to form 3-(2-methyl-5-nitro-4-oxoquinazolin-3(4H)-yl)piperidine-2,6-dione; and (c) reducing 3-(2-methyl-5-nitro-4-oxoquinazolin-3(4H)-yl)piperidine-2,6-dione in a solvent to form 3-(5-amino-2-methyl-4-oxoquinazolin-3(4H)-yl)piperidine-2,6-dione, or an enantiomer or a mixture of enantiomers thereof or a pharmaceutically acceptable salt, solvate, hydrate, or polymorph thereof.

In certain embodiments, steps (b) (i.e., reacting 2-methyl-5-nitro-4H-benzo[d][1,3]oxazin-4-one with 3-aminopiperidine-2,6-dione) and (c) (i.e., reducing 3-(2-methyl-5-nitro-4-oxoquinazolin-3(4H)-yl)piperidine-2,6-dione) are performed as described herein elsewhere.

In certain embodiments, the activated acetic acid is acetyl halide. In certain embodiments, the activated acetic acid is acetyl chloride, acetyl bromide, acetyl iodide, or a mixture thereof. In certain embodiments, the activated acetic acid is acetyl chloride. In certain embodiments, the activated acetic acid is acetyl bromide. In certain embodiments, the activated acetic acid is acetyl iodide. In certain embodiments, the activated acetic acid is acetic anhydride. In certain embodiments, the activated acetic acid is a thioester of acetic acid.

In certain embodiments, the molar ratio of the activated acetic acid versus 2-amino-6-nitrobenzoic acid in step (a) (i.e., reacting 2-amino-6-nitrobenzoic acid with acetic anhydride in a solvent to form 2-methyl-5-nitro-4H-benzo[d][1,3] oxazin-4-one) is ranging from about 1 to about 10. In certain embodiments, the molar ratio of the activated acetic acid versus 2-amino-6-nitrobenzoic acid in step (a) is ranging from about 1 to about 5. In certain embodiments, the molar ratio of the activated acetic acid versus 2-amino-6-nitrobenzoic acid in step (a) is ranging from about 1.5 to about 5. In certain embodiments, the molar ratio of the activated acetic acid versus 2-amino-6-nitrobenzoic acid in step (a) is ranging from about 1.5 to about 2.5. In certain embodiments, the molar ratio of the activated acetic acid versus 2-amino-6-nitrobenzoic acid in step (a) is about 1.5, about 1.6, about 1.7, about 1.8, about 1.9, about 2, about 2.1, about 2.2, about 2.3, about 2.4, about 2.5, about 2.6, about 2.7, about 2.8, about 2.9, or about 3. In certain embodiments, the molar ratio of the activated acetic acid versus 2-amino-6-nitrobenzoic acid in step (a) is about 1.5. In certain embodiments, the molar ratio of the activated acetic acid versus 2-amino-6-nitrobenzoic acid in step (a) is about 1.6. In certain embodiments, the molar ratio of the activated acetic acid versus 2-amino-6-nitrobenzoic acid in step (a) is about 1.7. In certain embodiments, the molar ratio of the activated acetic acid versus 2-amino-6-nitrobenzoic acid in step (a) is about 1.8. In certain embodiments, the molar ratio of the activated acetic acid versus 2-amino-6-nitrobenzoic acid in step (a) is about 1.9. In certain embodiments, the molar ratio of the activated acetic acid versus 2-amino-6-nitrobenzoic acid in step (a) is about 2. In certain embodiments, the molar ratio of the activated acetic acid versus 2-amino-6-nitrobenzoic acid in step (a) is about 2.1. In certain embodiments, the molar ratio of the activated acetic acid versus 2-amino-6-nitrobenzoic acid in step (a) is about 2.2. In certain embodiments, the molar ratio of the activated acetic acid versus 2-amino-6-nitrobenzoic acid in step (a) is about 2.3. In certain embodiments, the molar ratio of the activated acetic acid versus 2-amino-6-nitrobenzoic acid in step (a) is about 2.4. In certain embodiments, the molar ratio of the activated acetic acid versus 2-amino-6-nitrobenzoic acid in step (a) is about 2.5. In certain embodiments, the molar ratio of the activated acetic acid versus 2-amino-6-nitrobenzoic acid in step (a) is about 2.6. In certain embodiments, the molar ratio of the activated acetic acid versus 2-amino-6-nitrobenzoic acid in step (a) is about 2.7. In certain embodiments, the molar ratio of the activated acetic acid versus 2-amino-6-nitrobenzoic acid in step (a) is about 2.8. In certain embodiments, the molar ratio of the activated acetic acid versus 2-amino-6-nitrobenzoic acid in step (a) is about 2.9. In certain embodiments, the molar ratio of the activated acetic acid versus 2-amino-6-nitrobenzoic acid in step (a) is about 3.

In certain embodiments, the solvent in step (a) (i.e., reacting 2-amino-6-nitrobenzoic acid with acetic anhydride in a solvent to form 2-methyl-5-nitro-4H-benzo[d][1,3]oxazin-4-one) is a hydrocarbon, chlorinated hydrocarbon, alcohol, ether, ketone, ester, carbonate, amide, nitrile, sulfoxide, sulfone, nitro compound, arene, heteroarene, heterocycle, carboxylic acid, phosphoramide, carbon sulfide, water, or a mixture thereof.

In certain embodiments, the solvent in step (a) (i.e., reacting 2-amino-6-nitrobenzoic acid with acetic anhydride in a solvent to form 2-methyl-5-nitro-4H-benzo[d][1,3]oxazin-4-one) is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in step (a) (i.e., reacting 2-amino-6-nitrobenzoic acid with acetic anhydride in a solvent to form 2-methyl-5-nitro-4H-benzo[d][1,3]oxazin-4-one) is a carboxylic acid ester. In certain embodiments, the solvent in step (a) is isopropyl acetate.

In certain embodiments, step (a) (i.e., reacting 2-amino-6-nitrobenzoic acid with acetic anhydride in a solvent to form 2-methyl-5-nitro-4H-benzo[d][1,3]oxazin-4-one) is conducted at a temperature ranging from about 50 to about 150° C., from about 75 to about 120° C., from about 75 to about 100° C., from about 80 to about 100° C., from about 80 to about 95° C., or from about 85 to about 90° C. In certain embodiments, step (a) is conducted at a temperature from about 85 to about 90° C.

In one particular embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-amino-6-nitrobenzoic acid with an activated acetic acid in a solvent to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; and (c) reducing 3-(2-methyl-5-nitro-4-oxoquinazolin-3(4H)-yl)piperidine-2,6-dione via transfer hydrogenation in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; and wherein steps (a), (b), and (c) are each as described herein elsewhere.

In yet another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-amino-6-nitrobenzoic acid with activated acetic acid in a solvent to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; and (c) reducing 3-(2-methyl-5-nitro-4-oxoquinazolin-3(4H)-yl)piperidine-2,6-dione via transfer hydrogenation in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof. In one aspect of the embodiment, the molar ratio of the activated acetic acid versus 2-amino-6-nitrobenzoic acid is ranging from about 1 to about 10, from about 1 to about 5, from about 1.5 to about 5, or from about 1.5 to about 2.5; and wherein steps (a), (b), and (c) are each as described herein elsewhere.

In yet another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the step of hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof.

In certain embodiments, the hydrolysis step is performed in the presence of a deformylation catalyst. In certain embodiments, the deformylation catalyst is an acid. In certain embodiments, the deformylation catalyst is an organic acid. In certain embodiments, the deformylation catalyst is an inorganic acid. In certain embodiments, the deformylation catalyst is hydrochloride.

In certain embodiments, the solvent in the deformylation step is a hydrocarbon, chlorinated hydrocarbon, alcohol, ether, ketone, ester, carbonate, amide, nitrile, sulfoxide, sulfone, nitro compound, heteroarene, heterocycle, carboxylic acid, phosphoramide, carbon sulfide, water, or a mixture thereof.

In certain embodiments, the solvent in the deformylation step is petroleum ether, pentane, hexane(s), heptane, octane, isooctane, cyclopentane, cyclohexane, methylcyclohexane, benzene, toluene, xylene, tetralin, cumene, dichloromethane (DCM), 1,2-dichloroethane, 1,1-dichloroethene, 1,2-dichloroethene, chloroform, trichloroethane, trichloroethene, carbon tetrachloride, chlorobenzene, trifluoromethylbenzene, methanol, ethanol, isopropanol (IPA), 1-propanol, 1-butanol, 2-butanol, t-butanol, 3-methyl-1-butanol, 1-pentanol, 2-methoxyethanol, 2-ethoxyethanol, ethyleneglycol, diethyl ether, diisopropyl ether, methyl t-butyl ether (MTBE), diphenyl ether, 1,2-dimethoxyethane, bi(2-methoxyethyl)ether, 1,1-dimethoxymethane, 2,2-dimethoxypropane, anisole, acetone, butanone, methyl ethyl ketone (MEK), methyl isopropyl ketone, methyl butyl ketone, methyl isobutyl ketone (MIBK), methyl acetate, ethyl formate, ethyl acetate, propyl acetate, isopropyl acetate, isobutyl acetate, butyl acetate, ethylene carbonate, propylene carbonate, formamide, N,N-dimethylformamide (DMF), N,N-dimethylacetamide, acetonitrile (ACN), dimethyl sulfoxide (DMSO), sulfolane, nitromethane, nitrobenzene, N-methyl pyrrolindone, 2-methyl tetrahydrofuran, tetrahydrofuran (THF), dioxane, pyridine, formic acid, acetic acid, trichloroacetic acid, trifluoroacetic acid, hexamethylphosphoramide, carbon sulfide, water; or a mixture thereof.

In certain embodiments, the solvent in the deformylation step comprises a $C_{1-6}$ alcohol. Without being limited by any theory, the alcohol acts as a reagent in the deformylation step. In certain embodiments, the solvent in the deformylation step comprises ethanol. In certain embodiments, the solvent in the deformylation step comprises a $C_{1-6}$ alcohol and water. In certain embodiments, the solvent in the deformylation step comprises ethanol and water. In certain embodiments, the solvent in the deformylation step comprises formic acid, a $C_{1-6}$ alcohol, and water. In certain embodiments, the solvent in the deformylation step comprises formic acid, ethanol, and water. In certain embodiments, the solvent in the deformylation step comprises formic acid, a $C_{1-6}$ alcohol, and water. In certain embodiments, the solvent in the deformylation step comprises formic acid, ethanol, and water. In certain embodiments, the solvent in the deformylation step is a mixture formic acid, a $C_{1-6}$ alcohol, and water. In certain embodiments, the solvent in the deformylation step is a mixture of formic acid, ethanol, and water.

In certain embodiments, the deformylation step is performed at a temperature ranging from about 50 to about 120° C., from about 60 to about 100° C., from about 60 to about 90° C., from or about 65 to about 85° C.

In another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof comprising the steps of (a) reducing 3-(2-methyl-5-nitro-4-oxoquinazolin-3(4H)-yl)piperidine-2,6-dione in a solvent in the presence of formic acid to form N-(3-(2,6-dioxopiperidin-3-yl)-2-methyl-4-oxo-3,4-dihydroquinazolin-5-yl)formamide; and (b) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; wherein steps (a) and (b) are each as described herein elsewhere.

In one embodiment, the reduction of 3-(2-methyl-5-nitro-4-oxoquinazolin-3(4H)-yl)piperidine-2,6-dione is performed in the presence of formic acid via transfer hydrogenation.

In yet another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-methyl-5-nitro-4H-benzo[d][1,3]oxazin-4-one with 3-aminopiperidine-2,6-dione or a salt thereof in a solvent to form 3-(2-methyl-5-nitro-4-oxoquinazolin-3(4H)-yl)piperidine-2,6-dione; (b) reducing 3-(2-methyl-5-nitro-4-oxoquinazolin-3(4H)-yl)piperidine-2,6-dione in a solvent in the presence of formic acid to form N-(3-(2,6-dioxopiperidin-3-yl)-2-methyl-4-oxo-3,4-dihydroquinazolin-5-yl)formamide; and (c) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; wherein steps (a), (b), and (c) are each as described herein elsewhere.

In one embodiment, the reduction of 3-(2-methyl-5-nitro-4-oxoquinazolin-3(4H)-yl)piperidine-2,6-dione is performed in a solvent in the presence of formic acid via transfer hydrogenation. In another embodiment, the reaction of 2-methyl-5-nitro-4H-benzo[d][1,3]oxazin-4-one with 3-aminopiperidine-2,6-dione or a salt thereof in a solvent is performed in the presence of a coupling reagent to form 3-(2-methyl-5-nitro-4-oxoquinazolin-3(4H)-yl)piperidine-2,6-dione.

In one particular embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; (b) reducing 3-(2-methyl-5-nitro-4-oxoquinazolin-3(4H)-yl)piperidine-2,6-dione in the presence of formic acid via transfer hydrogenation in a solvent to form N-(3-(2,6-dioxopiperidin-3-yl)-2-methyl-4-oxo-3,4-dihydroquinazolin-5-yl)formamide; and (c) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; wherein steps (a), (b), and (c) are each as described herein elsewhere.

In another embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-amino-6-nitrobenzoic acid with an activated acetic acid in a solvent to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione or a salt thereof in a solvent to form 3-(2-methyl-5-nitro-4-oxoquinazolin-3(4H)-yl)piperidine-2,6-dione; (c) reducing 3-(2-methyl-5-nitro-4-oxoquinazolin-3(4H)-yl)piperidine-2,6-dione in a solvent in the presence of formic acid to form N-(3-(2,6-dioxopiperidin-3-yl)-2-methyl-4-oxo-3,4-dihydroquinazolin-5-yl)formamide; and (d) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; wherein steps (a), (b), (c), and (d) are each as described herein elsewhere.

In one embodiment, the reduction of 3-(2-methyl-5-nitro-4-oxoquinazolin-3(4H)-yl)piperidine-2,6-dione is performed in a solvent in the presence of formic acid via transfer hydrogenation.

In another embodiment, the reaction of 2-methyl-5-nitro-4H-benzo[d][1,3]oxazin-4-one with 3-aminopiperidine-2,6-dione or a salt thereof is performed in a solvent in the present of a coupling reagent.

In one particular embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-amino-6-nitrobenzoic acid with an activated acetic acid in a solvent to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; (c) reducing 3-(2-methyl-5-nitro-4-oxoquinazolin-3(4H)-yl)piperidine-2,6-dione in a solvent in the presence of formic acid via transfer hydrogenation to form N-(3-(2,6-dioxopiperidin-3-yl)-2-methyl-4-oxo-3,4-dihydroquinazolin-5-yl)formamide; and (d) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; wherein steps (a), (b), (c), and (d) are each as described herein elsewhere.

In one embodiment, the molar ratio of the activated acetic acid versus 2-amino-6-nitrobenzoic acid is ranging from about 1 to about 10, from about 1 to about 5, from about 1.5 to about 5, or from about 1.5 to about 2.5.

In one specific embodiment, provided herein is a method for preparing 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof; comprising the steps of (a) reacting 2-amino-6-nitrobenzoic acid with an activated acetic acid in a solvent to form 2-methyl-5-nitro-4H-benzo[d][1,3]oxazin-4-one; (b) reacting 2-methyl-5-nitro-4H-benzo[d][1,3]oxazin-4-one with 3-aminopiperidine-2,6-dione or a salt thereof in a solvent in the presence of a coupling reagent to form 3-(2-methyl-5-nitro-4-oxoquinazolin-3(4H)-yl)piperidine-2,6-dione; (c) reducing 3-(2-methyl-5-nitro-4-oxoquinazolin-3(4H)-yl)piperidine-2,6-dione in a solvent in the presence of formic acid via transfer hydrogenation to form N-(3-(2,6-dioxopiperidin-3-yl)-2-methyl-4-oxo-3,4-dihydroquinazolin-5-yl)formamide; and (d) hydrolyzing N-(3-(2,6-dioxopiperidin-3-yl)-2-methyl-4-oxo-3,4-dihydroquinazolin-5-yl)formamide in a solvent to form 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof wherein the molar ratio of the activated acetic acid versus 2-amino-6-nitrobenzoic acid is ranging from about 1 to about 10, from about 1 to about 5, from about 1.5 to about 5, or from about 1.5 to about 2.5; and wherein steps (a), (b), (c), and (d) are each as described herein elsewhere.

In certain embodiments, the methods provided herein are for the preparation of a pharmaceutically acceptable salt of 3-(5-amino-2-methyl-4-oxoquinazolin-3(4H)-yl)piperidine-2,6-dione, or an enantiomer or a mixture of enantiomers thereof; or a solvate, hydrate, or polymorph thereof. In certain embodiments, the methods provided herein are for the preparation of a hydrochloride salt of 3-(5-amino-2-methyl-4-oxoquinazolin-3(4H)-yl)piperidine-2,6-dione, or an enantiomer or a mixture of enantiomers thereof; or a solvate, hydrate, or polymorph thereof. In certain embodiments, the methods provided herein are for the preparation of 3-(5-amino-2-methyl-4-oxoquinazolin-3(4H)-yl)piperidine-2,6-dione hydrochloride, or a solvate, hydrate, or polymorph thereof. In certain embodiments, the methods provided herein are for the preparation of a polymorph of 3-(5-amino-2-methyl-4-oxoquinazolin-3(4H)-yl)piperidine-2,6-dione hydrochloride, or a solvate or hydrate polymorph thereof. In certain embodiments, the methods provided herein are for the preparation of a polymorph of 3-(5-amino-2-methyl-4-oxoquinazolin-3(4H)-yl)piperidine-2,6-dione hydrochloride. In certain embodiments, the methods provided herein are for the preparation of Form A of 3-(5-amino-2-methyl-4-oxoquinazolin-3(4H)-yl)piperidine-2,6-dione hydrochloride, which is described in U.S. Provisional App. No. 61/451,806, filed Mar. 11, 2011; the disclosure of which is incorporated herein by reference in its entirety.

In certain embodiments, the overall yield of the methods provided herein for the preparation of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof is no less than about 30%, no less than about 40%, no less than about 50%, no less than about 55%, no less than about 60%, no less than about 65%, no less than about 70%, no less than about 75%, no less than about 80%, no less than about 85%, no less than about 90%, or no less than about 95%, wherein the yield is calculated based on starting material.

In certain embodiments, 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof prepared by the methods provided herein is substantially pure. In certain embodiments, 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof prepared by the methods provided herein is suitable for use in humans, such as for treating, preventing, and/or managing a disease, disorder, or condition.

In certain embodiments, 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof prepared by the methods provided herein has a purity of no less than about 95% by weight, no less than about 96% by weight, no less than about 97% by weight, no less than about 97.5% by weight, no less than about 98% by weight, no less than about 98.5% by weight, no less than about 99% by weight, no less than about 99.5% by weight, or no less than about 99.9% by weight.

In certain embodiments, the total impurities in 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof prepared by the methods provided herein are no greater than about 5% by weight, no greater than about 4% by weight, no greater than about 3% by weight, no greater than about 2.5% by weight, no greater than about 2% by weight, no greater than about 1.5% by weight, no greater than about 1% by weight, no greater than about 0.5% by weight, or no greater than about 0.1% by weight.

In certain embodiments, the impurity is detectable by HPLC (high performance liquid chromatography). In certain embodiments, the impurity includes, but is not limited to, 2-acetamido-6-nitrobenzoic acid, N-(3-(2,6-dioxopiperidin-3-yl)-2-methyl-4-oxo-3,4-dihydroquinazolin-5-yl)formamide, and 3-(2-methyl-4-oxoquinazolin-3(4H)-yl)piperidine-2,6-dione. In certain embodiments, the impurity is 2-acetamido-6-nitrobenzoic acid. In certain embodiments, the impurity is N-(3-(2,6-dioxopiperidin-3-yl)-2-methyl-4-oxo-3,4-dihydroquinazolin-5-yl)formamide. In certain embodiments, the impurity is 3-(2-methyl-4-oxoquinazolin-3(4H)-yl)piperidine-2,6-dione.

In certain embodiments, the impurity is a metal based impurity. In certain embodiments, the impurity is palladium. In certain embodiments, the impurity is a volatile organic compound. In certain embodiments, the impurity is an organic solvent. In certain embodiments, the impurity is acetonitrile, formic acid, methanol, ethanol, or propanol. In certain embodiments, the impurity is acetonitrile, formic acid, methanol, ethanol, or isopropanol.

In certain embodiments, the weight loss on drying (LOD) of 3-(5-amino-2-methyl-4-oxoquinazolin-3(4H)-yl)piperidine-2,6-dione, or an enantiomer or a mixture of enantiomers thereof; or a pharmaceutically acceptable salt, solvate, hydrate, or polymorph thereof prepared by the methods provided herein is no greater than about 5% by weight, no greater than about 4% by weight, no greater than about 3% by weight, no greater than about 2% by weight, no greater than about 1% by weight, no greater than about 0.9% by weight, no greater than about 0.8% by weight, no greater than about 0.7% by weight, no greater than about 0.6% by weight, no greater than about 0.5% by weight, no greater than about 0.4% by weight, no greater than about 0.3% by weight, no greater than about 0.2% by weight, or no greater than about 0.1% by weight.

2. Preparation of N-(3-(2,6-dioxopiperidin-3-yl)-2-methyl-4-oxo-3,4-dihydroquinazolin-5-yl)formamide In one embodiment, provided herein is a method for preparing 3 N-(3-(2,6-dioxopiperidin-3-yl)-2-methyl-4-oxo-3,4-dihydroquinazolin-5-yl)formamide, or an enantiomer or a mixture of enantiomers thereof or a solvate, hydrate, or polymorph thereof comprising the step of reducing 3-(2-methyl-5-nitro-4-oxoquinazolin-3(4H)-yl)piperidine-2,6-dione in the presence of formic acid to form N-(3-(2,6-dioxopiperidin-3-yl)-2-methyl-4-oxo-3,4-dihydroquinazolin-5-yl)formamide, or an enantiomer or a mixture of enantiomers thereof or a solvate, hydrate, or polymorph thereof, as described herein elsewhere.

In another embodiment, provided herein is a method for preparing 3 N-(3-(2,6-dioxopiperidin-3-yl)-2-methyl-4-oxo-3,4-dihydroquinazolin-5-yl)formamide, or an enantiomer or a mixture of enantiomers thereof or a solvate, hydrate, or polymorph thereof comprising the step of reducing 3-(2-methyl-5-nitro-4-oxoquinazolin-3(4H)-yl)piperidine-2,6-dione in the presence of formic acid via transfer hydrogenation in a solvent to form N-(3-(2,6-dioxopiperidin-3-yl)-2-methyl-4-oxo-3,4-dihydroquinazolin-5-yl)formamide, or an enantiomer or a mixture of enantiomers thereof or a solvate, hydrate, or polymorph thereof, as described herein elsewhere.

C. Compound

In one embodiment, provided herein is N-(3-(2,6-dioxopiperidin-3-yl)-2-methyl-4-oxo-3,4-dihydroquinazolin-5-yl)formamide, or an enantiomer or a mixture of enantiomers thereof or a solvate, hydrate, or polymorph thereof. In another embodiment, provided herein is N-(3-(2,6-dioxopiperidin-3-yl)-2-methyl-4-oxo-3,4-dihydroquinazolin-5-yl)formamide.

VI. EXAMPLES

Certain embodiments are illustrated by the following non-limiting examples.

In the examples below, unless otherwise indicated, all temperatures are set forth in degrees Celsius and all parts and percentages are by weight. Reagents may be purchased from commercial suppliers, such as, e.g., Sigma-Aldrich® Chemical Co., and may be used without further purification unless otherwise indicated. Reagents may also be prepared following standard literature procedures known to those skilled in the art. Solvents may be purchased, for example, from Sigma-Aldrich®, and may be used as received or may be purified using standard methods known to those skilled in the art, unless otherwise indicated.

Unless otherwise specified, the reactions set forth below were done generally at ambient temperature or room temperature. Reactions were assayed by HPLC, and terminated as judged by the consumption of starting material.

The compound structures and purities in the examples below were confirmed by one or more of the following methods: proton nuclear magnetic resonance ($^1$H NMR) spectroscopy, $^{13}$C NMR spectroscopy, mass spectroscopy, infrared spectroscopy, melting point, X-ray crystallography, and/or HPLC. $^1$H NMR spectra were determined using a NMR spectrometer operating at a certain field strength. Chemical shifts are reported in parts per million (ppm, δ) downfield from a standard, e.g., an internal standard, such as TMS. Alternatively, $^1$H NMR spectra were referenced to signals from residual protons in deuterated solvents as follows: $CDCl_3$=7.25 ppm; $DMSO_{d6}$=2.49 ppm; $C_6D_6$=7.16 ppm; $CD_3OD$=3.30 ppm. Peak multiplicities are designated as follows: s, singlet; d, doublet; dd, doublet of doublets; t, triplet; dt, doublet of triplets; q, quartet; br, broadened; and m, multiplet. Coupling constants are given in Hertz (Hz). Mass spectra (MS) data were obtained using a mass spectrometer with APCI or ESI ionization.

Example 1

Preparation of Form A of 3-(5-amino-2-methyl-4-oxoquinazolin-3(4H)-yl)piperidine-2,6-dione hydrochloride 4

A. Preparation of 2-methyl-5-nitro-4H-benzo[d][1,3]oxazin-4-one 2

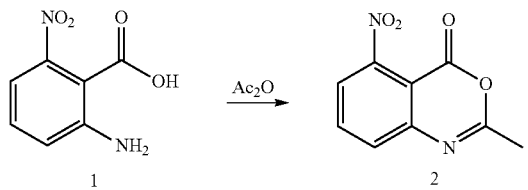

2-Amino-6-nitrobenzoic acid 1 was treated with acetic anhydride (2.2 equiv.) in isopropyl acetate (5× vol. relative to compound 1) in a reactor at 85-90° C. After 19 hrs, heptane (5× vol. relative to compound 1) was charged as an antisolvent over 1.5 hrs at 70-80° C. The reaction mixture was then cooled to 0-5° C. The resulting solid was filtered and washed with heptane (2.5× vol.) twice to afford 2-methyl-5-nitro-4H-benzo[d][1,3]oxazin-4-one 2: HPLC purity: 97.25-99.31%.

Reagent Selection.

Acetic anhydride was selected as an acylation and dehydration reagent. Initially, compound 1 was refluxed in neat acetic anhydride (4.8 equivalents), followed by cooling and filtration to provide compound 2, which contained 5 wt % of acetic acid and was converted to an acetylated compound 1,2-acetamido-6-nitrobenzoic acid 1a, over a three month period under ambient storage in a glass bottle. In order to improve the stability of compound 2, the amount of acetic anhydride was reduced to 2.2 equivalents and isopropyl acetate was used as an alternative solvent.

Reaction of compound 1 with acetyl chloride and base, such as $Et_3N$, Hunig's Base, or imidazole in either acetonitrile or tetrahydrofuran at either room temperature or 45° C. provided compound 1a.

B. Preparation of 3-(2-methyl-5-nitro-4-oxoquinazolin-3(4H)-yl)piperidine-2,6-dione 4

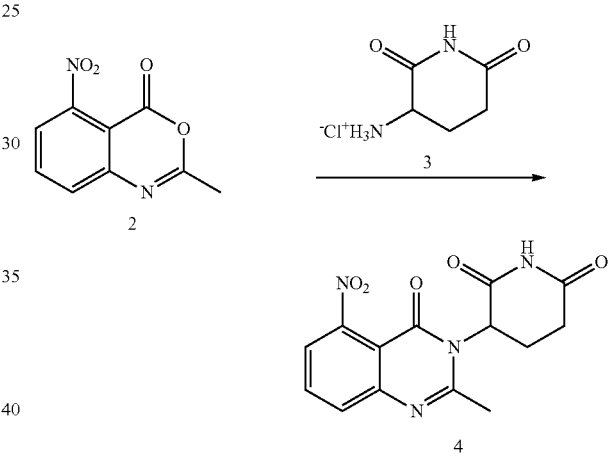

A slurry of compound 2 was treated with 3-aminopiperidine-2,6-dione hydrochloride 3 (1.1 equiv.) in acetonitrile and a solution of 1-propanephosphonic acid cyclic anhydride ("T3P") (2 equiv.) in ethyl acetate at 75-80° C. After 3 to 5 days, the total of compounds 1a and 2 was less than 1% area normalized (typically 0.05% area normalized). The reaction mixture was cooled to 55 to 65° C. Water was charged over 30 min, maintaining the temperature at 60° C. throughout the addition. During the first portion of water addition, an exotherm was observed. The mixture was further cooled to 20 to 30° C. over 1 hr. The resulting solid was filtered and washed with a mixture of acetonitrile and water (1:1). The solid was transferred back to the reactor and was agitated with a mixture of acetonitrile and water (1:1) between 20 to 30° C. for 1 hr. The mixture was filtered and the filter cake was washed with a mixture of acetonitrile and water (1:1). The filter cake was dried in a vacuum oven to afford compound 4 as a white solid: HPLC purity: 98.9 to 99.2%; yield: 89 to 93%; MS (m/e): 317 (M+1).

Alternatively, the conversion of 2-methyl-5-nitro-4H-benzo[d][1,3]oxazin-4-one to 3-(2-methyl-5-nitro-4-oxoquinazolin-3(4H)-yl)piperidine-2,6-dione was achieved using a mixture $POCl_3$ and water. A slurry of 2-methyl-5-nitro-4H-benzo[d][1,3]oxazin-4-one and 1.1 equiv of 3-aminopiperidine-2,6-dione hydrochloride in NMP (10× vol.) was charged to a reactor at 20-25° C., followed by the addition of 3 equiv. of water over 30 min at a temperature of no greater than 35° C. POCl₃ (2.1 equiv.) was then charged to the reactor over 30 min to 1 hr at a temperature of no greater than 55-60° C. After 1 hr at 55-60° C., 1 equiv. of DIPEA was charged to the reactor over 30 min at a temperature of no greater than 55-60° C. The reaction mixture was agitated at 55-60° C. After 1-2 days, IPC showed that the sum of 2-methyl-5-nitro-4H-benzo[d][1,3]oxazin-4-one and compound 1a was less than 3.5% area normalized (typically 2.5-3.5% area normalized). Water (5-10× vol.) was added over 30 min at a temperature of no greater than 55-60° C. The reaction mixture was cooled to 20-25° C. over 1-6 hrs; and then filtered. The reactor was rinsed with a mixture of NMP and water (1:1) (10× vol.). The batch was washed with the rinse, a mixture of NMP:water (1:1) (5× vol), and water (5× vol). The filter cake was dried in a vacuum oven to provide 3-(2-methyl-5-nitro-4-oxoquinazolin-3(4H)-yl)piperidine-2,6-dione in 80% yield.

Other phosphorus reagents, such as PCl₃ and PCl₅, provided compound 4 in a lower solution yield (2-25% yield) than T3P under the same reaction conditions. Replacing T3P with a combination of acetic anhydride and phosphoric acid provided compound 4 in 60% solution yield.

A coupling reagent, such as EDCI, with imidazole in DMF, provided compound 4 in 50% solution yield. Various acids, such as TFA, polyphosphoric acid, CSA, MsOH, and formic acid, with or without sodium hydrogen carbonate in acetonitrile at 70° C. did not provide compound 4. Bases, such as sodium hydrogen carbonate, sodium carbonate, sodium citrate dihydrate, sodium acetate, and imidazole, alone with compounds 2 and 3 provided compound 4 typically less than 20% area after 20 hrs at 70° C., and the reaction mixtures contained a significant amount of impurity peaks.

C. Preparation of 3-(5-amino-2-methyl-4-oxoquinazolin-3(4H)-yl)piperidine-2,6-dione hydrochloride 5

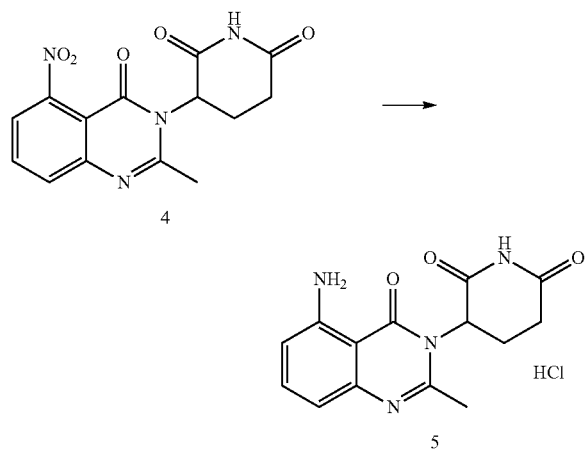

Conversion of compound 4 to 3-(5-amino-2-methyl-4-oxoquinazolin-3(4H)-yl)piperidine-2,6-dione 5 utilized a formic acid-mediated transfer hydrogenation of the nitro group to an amine. Compound 4 and 10% Pd—C (50% wet, 0.05× wt.) were charged to a reactor, followed by 2.5 volumes of water. The reaction mixture was cooled to 10 to 20° C. while 2.5 volumes of formic acid were charged over 2 hrs. The reaction mixture was ramped to 35 to 40° C. over 2 hrs. The reaction mixture was agitated at 35 to 40° C. until the reduction reaction was complete, typically taking from 3 to 5 hrs.

Under these conditions, N-(3-(2,6-dioxopiperidin-3-yl)-2-methyl-4-oxo-3,4-dihydroquinazolin-5-yl)formamide 5a was also detected during the reaction. Without being limited by any theory, compound 5 thus formed in the reaction mixture was partially converted to through the acylation of compound 5 by the excess formic acid present. ¹H NMR (DMSO-$d_6$) δ 2.23 (s, 1H), 2.66 (s, 5H), 5.16-5.53 (m, 1H), 7.22-7.41 (m, 1H), 7.66-7.87 (m, 1H), 8.47-8.68 (m, 1H), 11.09 (s, 1H), 11.60 (br s 1H).

Once the reduction was determined to be complete, the reaction mixture was filtered between 35 to 45° C. to remove the catalyst and then warmed to 50 to 60° C. Then, 6N HCl (1× vol.) was charged, followed by 10 volumes of ethanol. The HCl served as a catalyst for deformylation and also formed a hydrochloride salt of compound 5. Without being limited by any theory, ethanol reacted with the formic acid present to form ethyl formate, which was readily distilled off. This has the net effect of pushing the equilibrium towards compound 5 and promoting the desired deformylation reaction. The reaction mixture was heated to reflux (68 to 70° C.) and distilled. As a result of the change in the solvent composition, the boiling point climbed during the distillation, and the temperature of the reaction mixture was allowed to rise to 78 to 82° C. When the temperature attained this set point, distillation was discontinued and the reaction mixture was held at reflux for 1 to 3 hrs.

The reaction mixture was then cooled to 20 to 30° C. and aged for 1 to 2 hrs. The resulting solid was filtered, washed with ethanol (2×2 volumes), and dried under vacuum to afford compound 5 in about 90% yield.

Reduction Procedure Selection.

It is desirable that this reduction process does not require the use of hydrogen gas, which poses safety concerns and requires the use of a specialized equipment. Thus, a transfer hydrogenation is preferred over the use of hydrogen gas. In addition to formic acid, other transfer hydrogenations were also examined, including using cyclohexene, 1-methylcyclohexene, NaH₂PO₂, ammonium formate, and potassium formate. These alternative transfer hydrogenations were successful when conducted in DMF or NMP.

D. Recrystallization of 3-(5-amino-2-methyl-4-oxoquinazolin-3(4H)-yl)piperidine-2,6-dione hydrochloride 5

Recrystallization of compound 5 was performed in 50% aqueous acetonitrile. A slurry of compound 5 in 19.2 volumes of 50% aqueous acetonitrile was heated to 60 to 70° C. with agitation to bring about dissolution. The solution was filtered using an in-line filter (0.45 μm) into a second reactor, maintaining the temperature at 60 to 70° C. The first reactor was rinsed with 1 volume of 50% aqueous acetonitrile, and the rinse was transferred through the in-line filter into the second reactor. The mixture was then cooled to 45° C. and seeded with compound 5 seeds (0.03× wt). The slurry was then aged at 45° C. for 30 min. HCl (6N, 1.71 volumes) was then added to the slurry over 3 hrs via an inline filter. The batch was cooled to 0° C. in a linear ramp over 4 hrs. The mixture was aged at 0° C. for 1 hr, and can be held at this temperature overnight.

The slurry is filtered and the cake was washed with acetonitrile (2×3 volumes). The cake was dried in a vacuum oven at 40° C. to afford compound 5 as a very light yellow to off-white solid. The crystals have an acicular morphology with typical length of 50-200 microns.

The embodiments described herein are intended to be merely exemplary, and those skilled in the art will recognize, or will be able to ascertain using no more than routine experimentation, numerous equivalents of specific compounds, materials, and procedures. All such equivalents are considered to be within the scope of the disclosure.

All of the patents, patent applications and publications referred to herein are incorporated herein in their entireties. Citation or identification of any reference in this application is not an admission that such reference is available as prior art to this application. The full scope of the disclosure is better understood with reference to the appended claims.

What is claimed:

1. N-(3-(2,6-Dioxopiperidin-3-yl)-2-methyl-4-oxo-3,4-dihydroquinazolin-5-yl)formamide, or an enantiomer or a mixture of enantiomers thereof; or a solvate, hydrate, or polymorph thereof.

2. N-(3-(2,6-Dioxopiperidin-3-yl)-2-methyl-4-oxo-3,4-dihydroquinazolin-5-yl)formamide, or an enantiomer or a mixture of enantiomers thereof.

3. N-(3-(2,6-Dioxopiperidin-3-yl)-2-methyl-4-oxo-3,4-dihydroquinazolin-5-yl)formamide.

* * * * *